United States Patent [19]

Rüttimann et al.

[11] Patent Number: 4,603,223
[45] Date of Patent: Jul. 29, 1986

[54] PROCESS FOR THE MANUFACTURE OF QUINONE DERIVATIVES

[75] Inventors: August Rüttimann, Arlesheim, Switzerland; George H. Büchi, Jackson, N.H.

[73] Assignee: Hoffmann-La Roche Inc., Nutley, N.J.

[21] Appl. No.: 634,000

[22] Filed: Jul. 24, 1984

[30] Foreign Application Priority Data

Jul. 28, 1983 [CH] Switzerland .................. 4143/83
May 16, 1984 [CH] Switzerland .................. 2398/84

[51] Int. Cl.$^4$ .......................................... C07C 49/252
[52] U.S. Cl. ............................... 568/326; 568/373; 568/347; 568/315
[58] Field of Search ................... 568/326, 373

[56] References Cited

U.S. PATENT DOCUMENTS

| 3,291,835 | 12/1966 | Fan | 568/373 |
|---|---|---|---|
| 3,476,546 | 11/1969 | Roberts et al. | 568/326 |
| 3,896,153 | 7/1975 | Sato et al. | 260/396 R |
| 4,058,568 | 11/1977 | Little et al. | 568/373 |
| 4,061,660 | 12/1977 | Kijima et al. | 280/396 R |
| 4,374,775 | 2/1983 | Dotz | 260/376 K |

FOREIGN PATENT DOCUMENTS

| 245731 | 7/1963 | Australia | 568/373 |
|---|---|---|---|
| 235827 | 8/1959 | Austria | 260/390 R |
| 905490 | 3/1954 | Fed. Rep. of Germany | 260/396 R |
| 1054085 | 4/1959 | Fed. Rep. of Germany | 260/390 R |

OTHER PUBLICATIONS

Chem. Abstract, 54: 2294j (1960).
Houben-Weyl, "Methoden der Organischen Chemie", 4, Auflage, Band V/1c: Kohlenwasserstoffe, Teil 3 (1970) Georg Thieme, Verlag, Stuttgart, p. 1028, Table 10.
Onishchenko, A. S., "Diene Synthesis," Israel Program for Scientific Translations, Jerusalem, 1964, pp. vii–viii and 300–303.

*Primary Examiner*—James H. Reamer
*Attorney, Agent, or Firm*—Jon S. Saxe; Bernard S. Leon; George W. Johnston

[57] ABSTRACT

A novel process for the manufacture of quinone derivatives is described.

In this process a compound of the formula

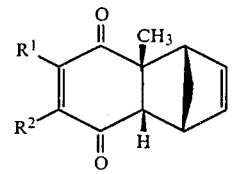

I is reacted with a compound of the formula

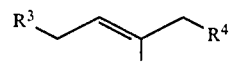

II and the resulting compound of the formula

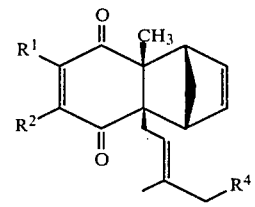

IV is subjected to a retro-Diels-Alder reaction. The substituents $R^1$, $R^2$, $R^3$ and $R^4$ have the significance given in the description.

1 Claim, No Drawings

PROCESS FOR THE MANUFACTURE OF QUINONE DERIVATIVES

BACKGROUND

1. Field of the Invention

The present invention is concerned with a novel process for the manufacture of quinone derivatives, especially of compounds of the vitamin K series and of ubiquinones. The invention is also concerned with novel starting materials and intermediates in this process.

2. Description

The hitherto known processes for the manufacture of such compounds normally start from hydroquinones or monoacylated hydroquinones and are therefore technically unsatisfactory, since a relatively large number of reaction steps must be carried out. Technically practicable processes starting from, for example, menadione itself or a readily accessible derivative thereof are hitherto unknown. This gap has now been closed by means of the process in accordance with the invention, since this permits vitamins of the K series as well as ubiquinones to be manufactured in one or two steps starting from readily accessible starting materials. Moreover, the process in accordance with the invention is of particular interest, since, in contrast to many previously known processes, it terminated with practically complete retention of the configuration of the double bond(s) in the side-chain.

SUMMARY OF THE INVENTION

The present invention concerns a process for preparing quinone derivatives. The inventive process comprises reacting a compound of the formula:

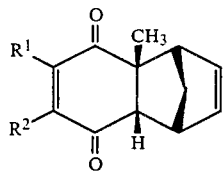

I wherein $R^1$ and $R^2$ each are methoxy or taken together are —CH=CH—CH=CH—,
with a compound of the formula

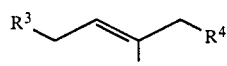

II wherein $R^3$ is a leaving group and $R^4$ is 3,7,11-trimethyldodecane or a group of the formula

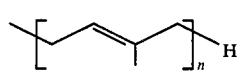

III in which n is an integer from 0 to 12,
and, if desired, converting a thus-obtained compound of the formula

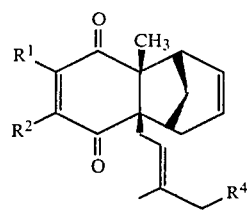

IV wherein $R^1$, $R^2$ and $R^4$ have the significance given above,
into a compound of the formula

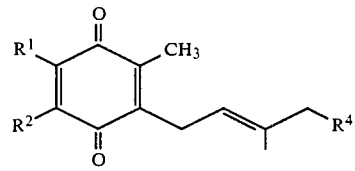

V wherein $R^1$, $R^2$ and $R^4$ have the significance given above.

DETAILED DESCRIPTION OF THE INVENTION

The present invention is concerned with a novel process for the manufacture of quinone derivatives, especially of compounds of the vitamin K series and of ubiquinones. The invention is also concerned with novel starting materials and intermediates in this process. More particularly, the present invention concerns a process for producing an intermediate of the formula

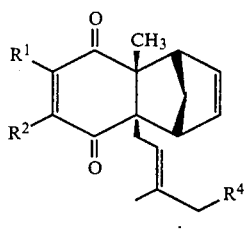

IV wherein $R^1$ and $R^2$ each are methoxy or when taken together are —CH=CH—CH=CH, and $R^4$ is 3,7,11-trimethyl-dodecane or a group of the formula

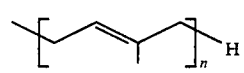

III in which n is an integer from 0 to 12.

In accordance with the present invention, a compound of the formula

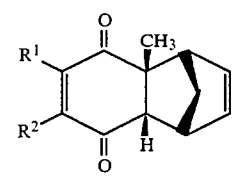

I wherein $R^1$ and $R^2$ are as above,
is reacted with a compound of the formula

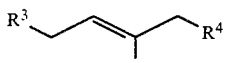

wherein $R^3$ is a leaving group and $R^4$ is as above, thereby to produce compound IV.

If desired compound IV can be converted to a compound of the formula

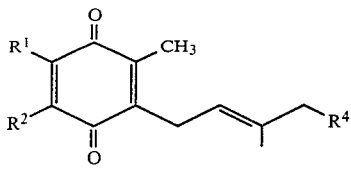

wherein $R^1$, $R^2$, and $R^4$ are as above.

Formula V represents compounds of the vitamin K series, such as $K_1$, $K_{2(5)}$, $K_{2(10)}$ etc. or ubiquinones, which are known compounds with known utility.

As used herein, the term "leaving group" denotes any conventional leaving groups which are commonly used in chemistry. More particularly, "leaving group" includes especially halogen such as fluorine, chlorine, bromine and iodine, with bromine and chlorine being preferred, or groups such as the mesyloxy group, the tosyloxy group, the acetate group and the like.

Alkali metal denotes lithium, sodium, potassium and rubidium.

In the pictorial representations of the compounds, the notation " ⊃ " signifies that the corresponding residue is situated above the plane of the molecule.

Unless otherwise indicated, all pictorial representations of appropriate compounds include cis/trans mixtures as well as corresponding cis and trans compounds.

The process in accordance with the invention permits the manufacture of trans/cis mixtures of the compounds of formulae IV and V, as well as the practically pure (E)- or (Z)-isomers depending on the configuration of the starting materials of formula II. Thus, for example, when a compound of formula II is used in the pure (E)-form, there can be obtained the corresponding compounds of formulae IV and V in practically pure (E)-form. When a compound of formula II is used in a cis/trans mixture, there can be obtained the corresponding compounds of formulae IV and V in cis/trans form.

The reaction of a compound of formula I with a compound of formula II can be carried out in an inert organic solvent which is inert under the reaction conditions and in the presence of a strong base. As solvents there come into consideration not only polar solvents but also apolar solvents. Apolar aprotic solvents such as, for example, aliphatic or aromatic hydrocarbons such as hexane, benzene, toluene and the like are preferred. The preferred polar protic solvent is tert.butanol. Mixtures of these solvents are also preferred. As strong bases there come into consideration in the scope of the present invention especially organic bases such as, for example, amides such as alkali metal amides (Li, Na K) or lithium dialkylamides, alcoholates such as alkali metal tert.butylates or hydrides such as sodium hydride or potassium hydride and the like. The reaction can be carried out at a temperature of about −20° C. to about +30° C., preferably at about −5° C. to about +10° C. and especially at about 0° C. to +5° C.

The compounds of formula IV are novel and also form an object of the present invention.

The conversion of a compound of formula IV into a compound of formula V is a retro-Diels-Alder reaction and can accordingly be carried out in a manner known per se. The heating can be carried out in the absence or in the presence of an inert solvent, for example at a temperature of about room temperature (about 23° C.) to about 200° C. preferably at a temperature of about 70° C. to about 120° C.

The compounds of formula II which are used as starting materials are known and can be prepared in a known manner.

The compounds of formula I which are used as starting materials in the process in accordance with the invention are novel and also form an object of the present invention. They can be prepared, for example, by reacting a quinone of the formula

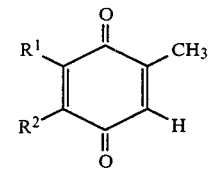

wherein $R^1$ and $R^2$ have the significance given above, with cyclopentadiene. This reaction can be carried out in an inert organic solvent and preferably at a temperature of about 0° C. to about 40° C., especially at room temperature. An organic acid such as, for example, acetic acid, propionic acid and the like is preferably used as the solvent.

The following examples illustrate the manufacture of the compounds provided by the invention and the preparation of starting materials. Unless otherwise stated, percentages and ratios relating to solvent mixtures are expressed in volume, purity data determined by gas chromatography are expressed in area %, and the remaining percentages and ratios are expressed in weight. Temperatures are in degrees Celsius (°C.), normal pressure is about 1 atmosphere, and room temperature is about 23° C. Unless indicated otherwise, the examples were carried out as written.

EXAMPLE 1

50 ml of tert.butanol/toluene (4:1) and 1.65 g (42 mmol) of potassium were placed under argon in a sulphonation flask equipped with a stirrer, a reflux condenser and argon gasification and heated at reflux for 1 hour. Thereupon, the mixture was cooled to 0° C. and treated with 5 g (21 mmol) of 1,4,4aα,9a-tetrahydro-9aα-methyl-1α,4α-methanoanthraquinone. The red solution obtained was stirred at 0° C. for a further 5 minutes. 8.7 g (1.15 eq.) of trans-phytyl bromide in 10 ml of tert.butanol/toluene (4:1) were subsequently added dropwise during about 15 minutes and the mixture was stirred at 0° C. for 1 hour. Thereupon, 15 ml of 3N HCl were added dropwise and the resulting yellow solution was stirred at room temperature for 0.5 hour. Thereupon, a 25% ammonia solution was added until the solution was orange. The solution was then concentrated on a rotary evaporator and extracted twice with hexane. The organic extracts were washed with saturated NaCl solution, dried over Na$_2$SO$_4$, filtered and concentrated. There were obtained 12.5 g of a brown oil which was chromatographed on a 400 g SiO$_2$ column with hexane/ethyl acetate (19:1). In this manner there were obtained 10.1 g of 1,4,4a,9a-tetrahydro-9aα-methyl-4aα-[3,7,11,15-tetramethyl-2-hexadecenyl]-1α,-4α-methanoanthraquinone in the form of a yellow oil.

10.1 g (19.6 mmol) of the previously obtained yellow oil were dissolved in about 25 ml of toluene and heated at reflux under argon in the dark for 15 minutes. The mixture was then cooled and concentrated on a rotary evaporator. There were obtained 9 g of a yellow oil which was chromatographed on a 300 g $SiO_2$ column with hexane/ethyl acetate (19:1). There were thus obtained 8.1 g of trans-vitamin $K_1$ in the form of a yellow oil.

HPLC: ratio trans/cis=96.1:3,9.

The ⌒ 1,4,4aα,9a-tetrahydro-9aα-methyl-1α,4α-methanoanthraquinone used as the starting material was prepared as follows:

103.6 g (0.6 mol) of menadione in 400 ml of acetic acid were placed in a flask. 126 ml (1.53 mol) of 1,3-cyclopentadiene were then added and the mixture was stirred at room temperature. All had dissolved after about 2.5 hours. After 4 days at room temperature the solution was concentrated on a rotary evaporator at 50° C., the residue was recrystallized at 0° C. from 280 ml of methanol, the crystals were filtered off and dried for 3 hours at 35° C. in a water-jet vacuum. There were obtained 121.6 g of 1,4,4aα,9a-tetrahydro-9aα-methyl-1α,-4α-methanoanthraquinone with a melting point of 95°–97° C.

In a manner analogous to the foregoing, starting from 1.8 g (7.5 mmol) of 1,4,4aα,9a-tetrahydro-9aαmethyl-1α,4α-methanoanthraquinone and 3.5 g (1.3 eq.) of cis-phytyl bromide there were obtained 1.83 g of cis-vitamin $K_1$ in the form of a yellow oil. HPLC content: 99% cis.

EXAMPLE 2

40 ml of tert.butanol and 1.65 g (42 mmol) of potassium were added under nitrogen to a 200 ml sulphonation flask equipped with a stirrer, a reflux condenser and argon gasification and heated at reflux for 1.5 hours. Thereupon, the mixture was cooled to room temperature and treated with 10 ml of toluene. The mixture was then cooled to +3° C. by means of an ice-bath. 5 g (21 mmol) of 1,4,4aα,9a-tetrahydro-9aα-methyl-1α,4α-methanoanthraquinone (prepared in accordance with Example 1) were then added and the mixture was stirred at +3° C. for 5 minutes. Thereupon, 9.8 g (27.3 mmol) of trans-phytyl bromide in 10 ml of tert.butanol/toluene (4:1) were added dropwise within 20 minutes at about 5° C. and the mixture was stirred at about +3° C. for a further 0.5 to 1 hour. 15 ml (45 mmol) of 3N HCl were subsequently added. The mixture was then warmed to +25° C. with a warm water-bath and stirred intensively at room temperature for 0.75 hour. Thereupon, 25% ammonia solution was added dropwise until the colour of the solution changed from pale yellow to orange. The solution was then concentrated on a rotary evaporator at 25°–30° C. The residue was taken up twice in 300 ml of hexane, washed once with semi-saturated NaCl solution and once with saturated NaCl solution and subsequently dried over $Na_2SO_4$. There were obtained 12.9 g of a yellow oil.

This oil was subsequently dissolved in 25 ml of toluene and heated at reflux for 15 minutes under argon in the dark. The mixture was then cooled and concentrated on a rotary evaporator at 35° C. There were obtained 12.5 g of a yellow-red oil which was chromatographed on 430 g of $SiO_2$ with hexane/ethyl acetate (19:1). There were obtained 8.6 g of trans-vitamin $K_1$ in the form of a yellow oil. HPLC: ratio trans/cis=96.6:3.4.

In a manner analogous to the foregoing, with the use of trans/cis-phytyl bromide there was obtained trans/cis-vitamin $K_1$. HPLC: ratio trans to cis=77 to 23.

EXAMPLE 3

In a manner analogous to Example 1 or 2, by reacting 1,4,4aα,9a-tetrahydro-9aα-methyl-1α,4α-methanoanthraquinone with (a) trans-phytyl chloride there was obtained trans-vitamin $K_1$.

HPLC: ratio trans to cis=98.3 to 1.7.

(b) with trans/cis-phytyl chloride there was obtained trans/cis-vitamin-$K_1$.

HPLC: ratio trans to cis=75 to 25.

EXAMPLE 4

4.7 g (42 mmol) of potassium tert.butylate in 40 ml of tert.butanol/toluene (4:1) were placed in a sulphonation flask equipped with a stirrer, a reflux condenser and argon gasification. After cooling the mixture to 0° C. 5.0 g (21 mmol) of 1,4,4aα,9a-tetrahydro-9aα-methyl-1α,-4α-methanoanthraquinone (prepared in accordance with Example 1) were added. The dark red mixture was subsequently stirred at 0° C. for a further 10 minutes. Thereupon, 3.4 g (22.8 mmol) of dimethylallyl bromide in 10 ml of tert.butanol/toluene (4:1) were added dropwise within 15 minutes and the mixture was stirred at 0° C. for a further 30 minutes. 20 ml of water were then added and the mixture was concentrated on a rotary evaporator. The residue was poured into 300 ml of semi-saturated NaCl solution, extracted with hexane, then washed with saturated NaCl solution, subsequently dried over $Na_2SO_4$ and then concentrated. There were obtained 6.5 g of 1,4,4a,9a-tetrahydro-9aα-methyl-4aα-(3-methyl-2-butenyl)-1α,4α-methanoanthraquinone in the form of yellow crystals.

For the recrystallization, these crystals were dissolved in 20 ml of ethanol, the solution was cooled firstly to 0° C. and then to −20° C. The separated crystals were filtered off and washed with ice-cold ethanol. The crystals were subsequently dried for 1 hour at 40° C. in a water-jet vacuum. There were obtained 4.4 g of pale yellow crystals with a melting point of 105°–106° C.

4.4 g of the previously mentioned pale yellow crystals were dissolved in 20 ml of toluene and heated at reflux under argon for 15 minutes. The mixture was subsequently cooled and concentrated on a rotary evaporator. There were obtained 4.1 g of a yellow oil which was chromatographed on a 125 g $SiO_2$ column with hexane/ethyl acetate (19:1). In this manner there were obtained 3.5 g of vitamin $K_{2(5)}$ as a yellow oil. HPLC content: 99%.

EXAMPLE 5

The following compounds were manufactured in a manner analogous to Example 4 starting from 1,4,4aα,-9a-tetrahydro-9aα-methyl-1α,4α-methanoanthraquinone:

By reaction with geranyl bromide the 4aα-[(E)-3,7-dimethyl-2,6-octadienyl]-1,4,4a,9a-tetrahydro-9aα-methyl-1α,4α-anthraquinone with a melting point of 68°–69° C., and therefrom vitamin $K_{2(10)}$ as yellow crystals with a melting point of 55°–56° C.; HPLC content: 99.4%, by reaction with farnesyl bromide with 1,4,4a9a-tetrahydro-9aα-methyl-4aα-[(all-E)-3,7,11-trimethyl-2,6,10-dodecatrienyl]-1α,4α-anthraquinone, and therefrom vitamin $K_{2(15)}$ as a yellow oil. HPLC content: 97.5%.

by reaction with geranylgeranyl bromide the 1,4,4a,9a-tetrahydro-9aα-methyl-4aα-[(all-E)-3,7,11,15-tetramethyl-2,6,10,14-hexadecatetraenyl]-1α,4α-methanoanthraquinone, and therefrom vitamin $K_{2(20)}$ in the form of yellow crystals with a melting point of 37° C. HPLC content: 96.3%.

by reaction with geranylfarnesyl bromide the 1,4,4a,9a-tetrahydro-9aα-methyl-4aα-[(all-E)-3,7,11,15,19-pentamethyl-2,6,10,14,18-eicosapentaenyl]-1α,4α-methanoanthraquinone as a yellow oil, and therefrom vitamin $K_{2(25)}$ as yellow crystals with a melting point of 43.5° C. HPLC content: 99.7%.

EXAMPLE 6

1.3 g (11.6 mmol) of potassium tert.butylate in 10 ml of tert.butanol/toluene (4:1) were placed under argon in a sulphonation flask equipped with a stirrer, a reflux condenser and argon gasification. Thereupon, the mixture was cooled to 0° C. and treated with 1.2 g (4.84 mmol) of 1,4,4a,8aα-tetrahydro-6,7-dimethoxy-4aα-methyl-1α,4α-methanonaphthalene-5,8-dione in 5 ml of tert.butanol/toluene (4:1). 2.3 g (6.3 mol) of trans-phytyl bromide in 5 ml of tert.butanol/toluene (4:1) were then added dropwise to the red solution obtained at 0° C. within 30 minutes. 10 ml of water were subsequently added to the mixture and the resulting mixture was evaporated on a rotary evaporator. The residue was extracted once with 200 ml of·hexane, the extract was washed once with water, then dried over sodium sulphate, filtered and the filtrate was concentrated. There were obtained 2.1 g of a brown oil which was chromatographed on a 70 g SiO2 column with hexane/ethyl acetate (4:1). There were thus obtained 600 mg of 1,4,4a,8a-Tetrahydro-6,7-dimethoxy-4aα-methyl-8aα-[(E)-3,7,11,15-tetramethyl-2-hexadecenyl]-1α,4α-methanonaphthalene-5,8-dione.

440 mg (0.84 mmol) of the previously obtained oil were dissolved in 3 ml of toluene and heated at reflux under argon for 15 minutes. The mixture was then cooled and concentrated on a rotary evaporator. 390 mg of a red oil were obtained. This oil was chromatographed on a 15 g SiO2 column with hexane/ethyl acetate (4:1). There were thus obtained 340 mg of phylloubiquinone as a red oil. HPLC content: 89%.

The 1,4,4a,8aα-tetrahydro-6,7-dimethoxy-4aα-methyl-1α,4α-methanonaphthalene-5,8-dione used as the starting material was prepared as follows:

1.0 g (5.49 mmol) of 2,3-dimethoxy-5-methyl-benzoquinone in 4 ml of acetic acid were placed in a flask. 1.4 ml (16.5 mmol) of 1,3-cyclopentadiene were then added and the mixture was stirred at room temperature. Thereupon, the solution was concentrated at 40° C. on a rotary evaporator, the residue was extracted twice with 200 ml of ether each time, the ether extract was washed three times with water and once with saturated sodium bicarbonate solution, then dried over $Na_2SO_4$, filtered and concentrated. There were obtained 1.5 g of 4aα,5,8,8a-tetrahydro-8aα-methyl-2,3-dimethoxy-5α,-8α-methanonaphthoquinone in the form of an orange coloured oil. This oil was chromatographed on a 45 g SiO2 column with hexane/ethyl acetate (2:1). This gave 1.23 g of pure 1,4,4a,8aα-tetrahydro-6,7-dimethoxy-4aα-methyl-1α,4α-methanonaphthalene-5,8-dione.

EXAMPLE 7

The following compounds were manufactured in a manner analogous to Example 6 starting from 1,4,4a,8aα-tetrahydro-6,7-dimethoxy-4aα-methyl-1α,4α-methanonaphthalene-5,8-dione:

by reaction with geranyl bromide the 4aα-[(E)-3,7-dimethyl-2,6-octadienyl]-1,4,4a,8a-tetrahydro-6,7-dimethoxy-8aα-methyl-1α,4α-methanonaphthalene-dione and therefrom 2,3-dimethoxy-5-methyl-6-[3,7-dimethyloctadien(2,6)-yl]benzoquinone-(1,4). HPLC purity: 100% trans, by reaction with geranylgeranyl bromide the 1,4,4a,8a-tetrahydro-6,7-dimethoxy-4aα-methyl-8aα-[(all-E)-3,7,11,15-tetramethyl-2,6,10,14-hexadecatetraenyl]-1α,4α-methanonaphthalene-5,8-dione and therefrom 2,3-dimethoxy-5-methyl-6-[3,7,11,15-tetramethyl-hexadecatetraen(2,6,10,14)-yl-(1)]-benzoquinone-(1,4). HPLC purity: 100% all-trans.

by reaction with geranylfarnesyl bromide the 1,4,4a,8a-tetrahydro-6,7-dimethoxy-4aα-methyl-8aα-[(all-E)-3,7,11,15,19-pentamethyl-2,6,10,14,18-eicosapentaenyl]-1α,4α-methanonaphthalene-5,8-dione and therefrom 2,3-dimethoxy-5-methyl-6-[3,7,11,15,19-pentamethyl-eicosapentaen-(2,6,10,14,18)-yl-(1)]-benzoquinone-(1,4). HPLC purity: 95.6% all-trans.

by reaction with solanesyl bromide the 1,4,4a,8a-tetrahydro-6,7-dimethoxy-8aα-methyl-4-aα-[(all-E)-3,7,11,15,19,23,27,31,35-nonamethyl-2,6,10,14,18,22,26,30,34-hexatriacontanonaenyl]-1α,4α-methanonaphthalene-5,8-dione and therefrom 2,3-dimethoxy-5-methyl-6-[3,7,11,15,19,23,27,31,35-nonamethyl-hexatrikontanonaen-(2,6,10,14,18,22,26,30,34)-yl-(1)]-benzoquinone-(1,4). HPLC purity: 98.7% all-trans.

We claim:

1. A compound of the formula

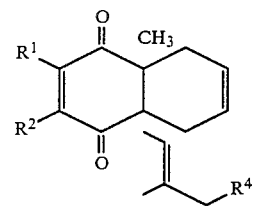

IV wherein $R^1$ and $R^2$ each are methoxy or when taken together are —CH=CH—CH=CH—, and $R^4$ is 3,7,11 trimethyl-dodecane or a group of the formula:

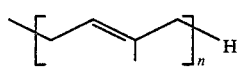

III in which n is an integer from 0–12, in any of its various cis and trans stereoisomeric forms and mixtures thereof.

* * * * *

UNITED STATES PATENT AND TRADEMARK OFFICE
CERTIFICATE OF CORRECTION

PATENT NO. : 4,603,223

DATED : July 29, 1986

Page 1 of 6

INVENTOR(S) : August Ruttimann and George H. Buchi

It is certified that error appears in the above-identified patent and that said Letters Patent is hereby corrected as shown below:

Column 1, lines 41-49, formula I

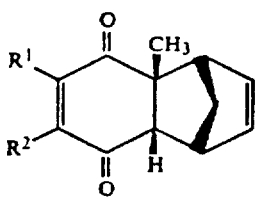

should read

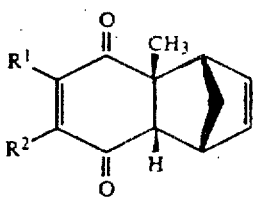

UNITED STATES PATENT AND TRADEMARK OFFICE
CERTIFICATE OF CORRECTION

PATENT NO. : 4,603,223
DATED : July 29, 1986
INVENTOR(S) : August Ruttimann and George H. Buchi It is certified that error appears in the above-identified patent and that said Letters Patent is hereby corrected as shown below:

Column 2, lines 1-10, formula IV

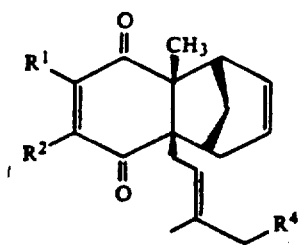

should read

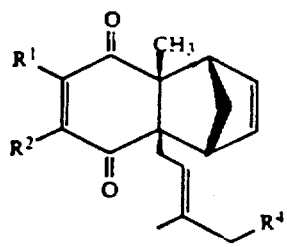

UNITED STATES PATENT AND TRADEMARK OFFICE
CERTIFICATE OF CORRECTION

PATENT NO. : 4,603,223
DATED : July 29, 1986
INVENTOR(S) : August Ruttimann and George H. Buchi It is certified that error appears in the above-identified patent and that said Letters Patent is hereby corrected as shown below:

Column 2, lines 35-45, formula IV

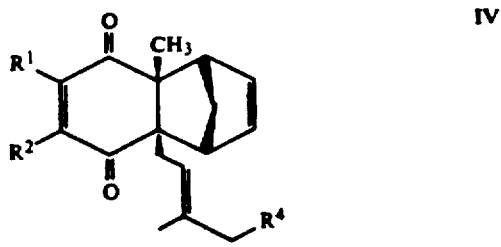

should read

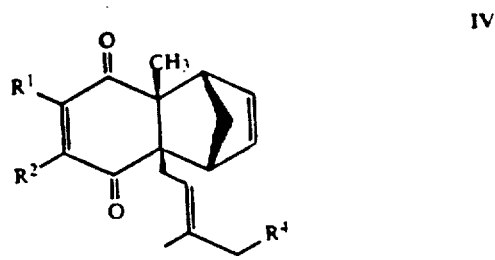

UNITED STATES PATENT AND TRADEMARK OFFICE
CERTIFICATE OF CORRECTION

PATENT NO. : 4,603,223

DATED : July 29, 1986

INVENTOR(S) : August Ruttimann and George H. Buchi

It is certified that error appears in the above-identified patent and that said Letters Patent is hereby corrected as shown below:

Column 2, lines 59-65, formula I

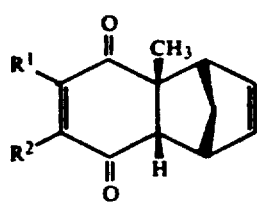

should read

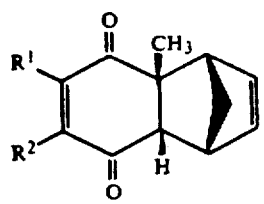

UNITED STATES PATENT AND TRADEMARK OFFICE
CERTIFICATE OF CORRECTION

PATENT NO. : 4,603,223

DATED : July 29, 1986

INVENTOR(S) : August Ruttimann and George H. Buchi

It is certified that error appears in the above—identified patent and that said Letters Patent is hereby corrected as shown below:

Claim 1, (Column 8, lines 44-53) formula IV

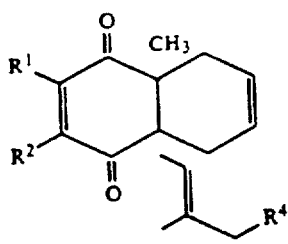

IV

UNITED STATES PATENT AND TRADEMARK OFFICE
CERTIFICATE OF CORRECTION

PATENT NO.   : 4,603,223
DATED        : July 29, 1986
INVENTOR(S)  : August Ruttimann and George H. Buchi It is certified that error appears in the above—identified patent and that said Letters Patent is hereby corrected as shown below:

should read

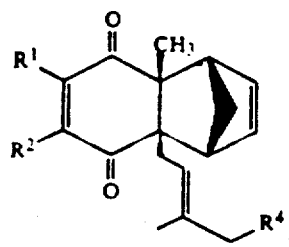

IV

Signed and Sealed this

Eleventh Day of November, 1986

Attest:

DONALD J. QUIGG

Attesting Officer     Commissioner of Patents and Trademarks